(12) United States Patent
Heuscher (10) Patent No.: US 8,897,413 B2
(45) Date of Patent: Nov. 25, 2014

(54) DYNAMIC ADJUSTABLE SOURCE COLLIMATION DURING FLY-BY SCANNING

(75) Inventor: Dominic J. Heuscher, Aurora, OH (US)

(73) Assignee: Koninklijke Philips N.V., Eindhoven (NL)

( * ) Notice: Subject to any disclaimer, the term of this patent is extended or adjusted under 35 U.S.C. 154(b) by 988 days.

(21) Appl. No.: 12/991,712

(22) PCT Filed: May 13, 2009

(86) PCT No.: PCT/IB2009/051986
§ 371 (c)(1),
(2), (4) Date: Nov. 9, 2010

(87) PCT Pub. No.: WO2009/141766
PCT Pub. Date: Nov. 26, 2009

(65) Prior Publication Data
US 2011/0058645 A1 Mar. 10, 2011

Related U.S. Application Data (60) Provisional application No. 61/054,823, filed on May 21, 2008.

(51) Int. Cl.
*A61B 6/03* (2006.01)
*A61B 6/06* (2006.01)
*A61B 6/00* (2006.01)
*A61B 6/02* (2006.01)

(52) U.S. Cl.
CPC .................. *A61B 6/032* (2013.01); *A61B 6/035* (2013.01); *A61B 6/06* (2013.01); *A61B 6/4085* (2013.01); *A61B 6/4476* (2013.01); *A61B 6/466* (2013.01); *A61B 6/503* (2013.01); *A61B 6/542* (2013.01); *A61B 6/027* (2013.01)
USPC .............................................. 378/15; 378/16

(58) Field of Classification Search
CPC ........ A61B 6/027; A61B 6/032; A61B 6/035; A61B 6/06; A61B 6/4085; A61B 6/4476; A61B 6/542
USPC ............................... 378/15, 16, 151, 152, 153
See application file for complete search history.

(56) References Cited

U.S. PATENT DOCUMENTS 6,023,494 A 2/2000 Senzig et al.
6,298,117 B1 10/2001 Hampel et al.
(Continued)

FOREIGN PATENT DOCUMENTS

| JP | 10314162 A | 12/1998 |
| JP | 2002102218 A | 4/2002 |
| WO | 2008042564 A1 | 4/2008 |

OTHER PUBLICATIONS

Huang, Q.; Medical Imaging Equipment; 2001; People's Health Publishing House; pp. 297.

*Primary Examiner* — Allen C. Ho (57) ABSTRACT

A medical imaging system (100) includes a radiation source (112) that rotates around an examination region about a longitudinal axis and emits radiation while translating in a direction of the longitudinal axis during a fly-by scan. A source collimator (114) collimates the emitted radiation during the fly-by scan to form a generally conical shaped radiation beam that traverses the examination region. The source collimator (114) dynamically varies collimation during the scan so as to increase and decrease a width of the radiation beam in the longitudinal axis direction during the scan. A detector array (122) detects radiation that traverses the examination region and generates signals indicative thereof. A reconstructor (126) reconstructs the signals to generate volumetric image data indicative of the examination region.

29 Claims, 7 Drawing Sheets

(56) References Cited

U.S. PATENT DOCUMENTS

| | | | |
|---|---|---|---|
| 6,322,248 B1* | 11/2001 | Yanagita et al. | 378/205 |
| 6,400,790 B1* | 6/2002 | Ohnesorge et al. | 378/15 |
| 6,683,935 B2* | 1/2004 | Moore | 378/17 |
| 6,990,170 B2* | 1/2006 | Sugihara et al. | 378/15 |
| 7,113,569 B2* | 9/2006 | Okumura et al. | 378/150 |
| 7,154,988 B2* | 12/2006 | Sugihara et al. | 378/15 |
| 7,170,975 B2* | 1/2007 | Distler et al. | 378/150 |
| 7,313,216 B2* | 12/2007 | Nishide et al. | 378/15 |
| 7,340,030 B2 | 3/2008 | Altman et al. | |
| 7,379,526 B2* | 5/2008 | Nishide et al. | 378/17 |
| 7,409,034 B2* | 8/2008 | Gohno | 378/7 |
| 7,508,903 B2* | 3/2009 | Nishide et al. | 378/15 |
| 7,639,774 B2* | 12/2009 | De Man et al. | 378/9 |
| 7,639,776 B2* | 12/2009 | Gohno et al. | 378/15 |
| 7,706,500 B2* | 4/2010 | Kondo | 378/15 |
| 7,983,385 B2* | 7/2011 | Heuscher et al. | 378/11 |
| 8,009,794 B2* | 8/2011 | Partain | 378/7 |
| 8,031,830 B2* | 10/2011 | Nakanishi | 378/15 |
| 8,094,775 B2* | 1/2012 | Noshi et al. | 378/15 |
| 8,213,568 B2* | 7/2012 | Heuscher et al. | 378/15 |
| 8,401,144 B2* | 3/2013 | Forthmann et al. | 378/19 |
| 8,467,494 B2* | 6/2013 | Brown et al. | 378/4 |
| 8,571,172 B2* | 10/2013 | Dafni et al. | 378/8 |
| 8,693,621 B2* | 4/2014 | Thran et al. | 378/17 |
| 2003/0031290 A1 | 2/2003 | Sugihara et al. | |
| 2005/0075563 A1 | 4/2005 | Sukovic et al. | |
| 2006/0039536 A1 | 2/2006 | Nishide et al. | |
| 2006/0177002 A1 | 8/2006 | Toth et al. | |
| 2007/0110211 A1 | 5/2007 | Hsieh et al. | |

* cited by examiner

DYNAMIC ADJUSTABLE SOURCE COLLIMATION DURING FLY-BY SCANNING

CROSS REFERENCE TO RELATED APPLICATIONS

This application claims the benefit of U.S. provisional application Ser. No. 61/054,823 filed May 21, 2008, which is incorporated herein by reference.

The following generally relates to dynamically adjusting beam width during a fly-by scan and finds particular application to computed tomography (CT). However, it is also amenable to other medical imaging applications and to non-medical imaging applications.

Conventional cone beam CT systems have included multi-slice detectors, which enable such systems to scan larger regions/volumes of interest in shorter periods of time relative to their single-slice system predecessors. Such scanning can be leveraged to quickly scan relatively larger regions of a patient and/or improve temporal resolution. However, conventional cone beam CT axial scans following a circular orbit are limited in that they do not acquire complete sampling for reconstruction (or fail to adequately sample portions of the scanned region/volume of interest). In general, at least 180 degrees plus a fan angle (or about 240 degrees) of data is needed for a 180 degree reconstruction. As a result of incomplete sampling, the reconstructed data will include cone beam artifact.

One approach for acquiring complete data with cone beam CT is to move the patient through the examination region via a patient support while the x-ray source rotates around the examination region. However, increases in rotating gantry speeds and the number of detector rows require relatively greater couch speeds, which complicates the mechanical implementation of patient support motion and may not be well-tolerated by some patients. Another approach is to sweep the focal spot through a saddle orbit. With this approach, the focal spot is cyclically and continuously swept along the z-axis direction at a frequency of two (2) cycles per gantry rotation (three hundred and sixty (360) degrees). Unfortunately, this results in a relatively larger source trajectory, which may require a larger detector. In addition, the saddle orbit requires relatively rapid acceleration and deceleration of the focal spot. Moreover, with the above techniques x-rays not used for reconstruction may traverse the patient, increasing patient dose.

Aspects of the present application address the above-referenced matters and others.

According to one aspect, a medical imaging system includes a radiation source that rotates around an examination region about a longitudinal axis and emits radiation while translating in a direction of the longitudinal axis during a fly-by scan. A source collimator collimates the emitted radiation during the fly-by scan to form a generally conical shaped radiation beam that traverses the examination region. The source collimator dynamically varies collimation during the scan so as to increase and decrease a width of the radiation beam in the longitudinal axis direction during the scan. A detector array detects radiation that traverses the examination region and generates signals indicative thereof. A reconstructor reconstructs the signals to generate volumetric image data indicative of the examination region.

According to another aspect, a medical imaging method comprises varying a beam angle of radiation beam emitted by an x-ray tube along a z-axis direction as the x-ray tube translates along the z-axis direction during a fly-by scan, wherein the beam angle increases as the x-ray tube moves from an initial position to an intermediate position and decreases as the x-ray tube moves from the intermediate position to a destination position.

According to another aspect, a computer readable storage medium containing instructions which, when executed by a computer, cause the computer to selectively vary a size of an aperture of a radiation source collimator in a z-axis direction during a fly-by scan performed with a medical imaging system in which a radiation source and the radiation source collimator translate in coordination from an initial position to a destination position, wherein the aperture determines a beam geometry of a radiation beam traversing a region of interest disposed in an examination region of the system.

According to another aspect, a computed tomography system performs fly-by scans gated by periodic motion of an organ being scanned.

The invention may take form in various components and arrangements of components, and in various steps and arrangements of steps. The drawings are only for purposes of illustrating the preferred embodiments and are not to be construed as limiting the invention.

Figure 1:
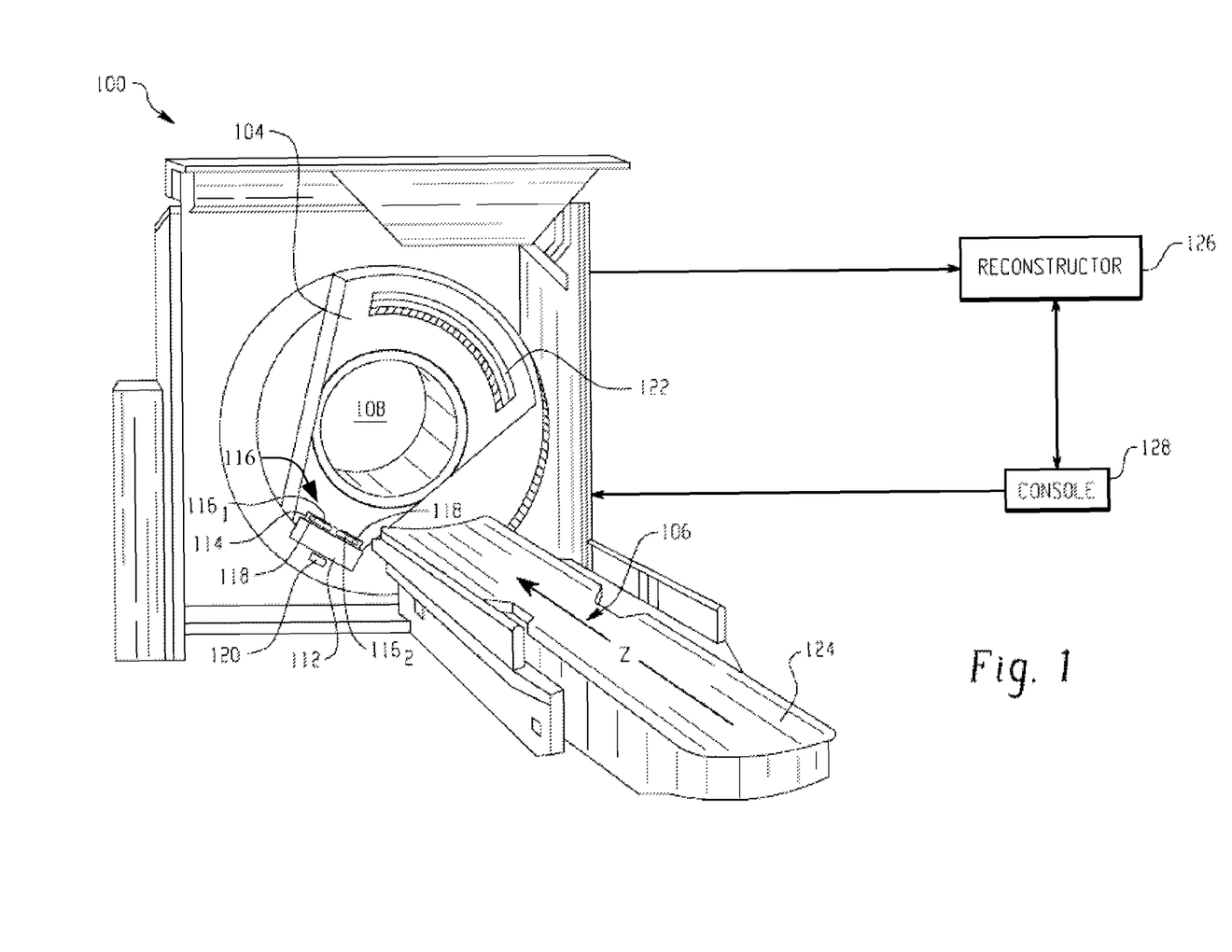
FIG. 1 illustrates an example imaging system.

With reference to FIG. 1, a CT imaging system 100 includes a rotating gantry portion 104 that rotates around an examination region 108 about a longitudinal or z-axis 106. The rotating gantry portion 104 supports a radiation source 112, such as an x-ray tube, that emits radiation that traverses the examination region 108.

The radiation source 112 is configured to physically translate in the z-axis direction before, during and/or after a helical or pilot scan. In this example, the radiation source 112 is configured to translate up to about forty (40) centimeters (cm) for a thirty-five (35) cm scan. In other embodiments, the radiation source 112 may be capable of translating greater or lesser distances. The radiation source 112 emits radiation while translating in the z-axis direction during a scan so as to perform a fly-by scan in which the radiation source 112 (and, hence the focal spot and the radiation beam) translates from a first or an initial position, through one or more intermediate positions, to a second or destination position, while an object disposed in the examination region is scanned. The radiation source 112 may travel in either direction along the z-axis. A non-limiting example of a suitable fly-by scanner is described in U.S. Pat. No. 7,983,385 B2 to Heuscher et al., filed Sep. 11, 2007, now U.S. Pat. No. 7,983,385 issued on Jul. 19, 2011, and entitled "Fly-By Scanning."

A source collimator 114, which translates in coordination with the radiation source 112, collimates the radiation emitted by the radiation source 112 to produce a generally conical shape radiation beam that traverses the examination region 108. For sake of brevity, the source collimator 114 is also referred to herein as the collimator 114. Varying collimating as such may be continuous or intermittent as the radiation source 112 and the source collimator 114 translate. The collimator 114 includes at least one collimator blade 116 configured to translate in the z-axis direction, relative to the radiation source 112. The CT imaging system 100 includes collimator blades $116_1$ and $116_2$. At least one drive 118 selectively drives or moves the at least one collimator blade 116 back and forth in the z-axis direction. A controller 120 controls the at least one drive 118 based on a scan protocol, including parameters such as the pitch of the helical trajectory (the distance the radiation source 112 travels per revolution of the radiation source 112), which may be variable or constant.

As described in greater detail below, in one instance the controller 120 controls the at least one drive 118 such that the at least one collimator blade 116 translates during a fly-by scan so as to cone down or decrease the beam angle of the radiation beam as the radiation source 112 travels towards either of the limits of travel and cone up or increase the beam angle of the radiation beam as the radiation source 112 travels towards a center of the examination region 108. Moving the at least one collimator blade 116 as such changes the aperture size of the collimator 114 in the z-axis direction and, hence, the width or angle of the beam traversing the examination region 108. If the radiation beam is coned down as the pitch decreases, relatively wider coverage can be achieved for a significantly smaller cone angle while capturing a complete data set (at least 180 degrees plus a fan angle of data) for reconstruction; a low pitch at the beginning of the scan, for example, during the first half-revolution, allows for a significantly smaller cone angle to capture a complete data set for reconstruction. In addition, coning down the radiation beam may reduce patient dose relative to a configuration where the radiation beam is not coned down.

The rotating gantry portion 104 also supports a radiation sensitive detector array 122, which is disposed about the rotating gantry portion 104 to subtend an angular arc opposite the radiation source 112. The detector array 122 includes a multi-slice detector having a plurality of detector elements extending in the axial and transverse directions. Each detector element detects radiation emitted by the radiation source 112 that traverses the examination region 108 and generates corresponding output signals or projection data indicative of the detected radiation. It is to be appreciated that the detector array 122 may or may not translate with the radiation source 112. With a configuration in which the source 112 and detector array 122 can move together, a relatively smaller detector array 122 and/or a two-dimensional anti-scatter grid can be used.

The CT imaging system 100 further includes a couch or patient support 124 that supports a human or object within the examination region 108. The patient support 124 is movable, which enables an operator or the system to suitably position the subject within the examination region 108 for scanning. Once suitably positioned within the examination region 108, the patient support 124 generally remains stationary during scanning. However, the patient support 124 moves during scanning when performing scout or pilot or otherwise, if desired.

The projection data generated by the detector array 122 is conveyed to a reconstructor 126, which reconstructs the projections and generates volumetric image data therefrom based on the scan protocol parameters, including the pitch. The image data is processed to generate one or more images of the scanned region of interest or a subset thereof.

An operator console 128 facilitates user interaction with the CT imaging system 100. Software applications executed by the operator console 128 allow the user to configure and/or control operation of the CT imaging system 100. For instance, the user can interact with the operator console 128 to select a fly-by scan protocol, and initiate, pause and/or terminate a fly-by scan.

Figure 2:
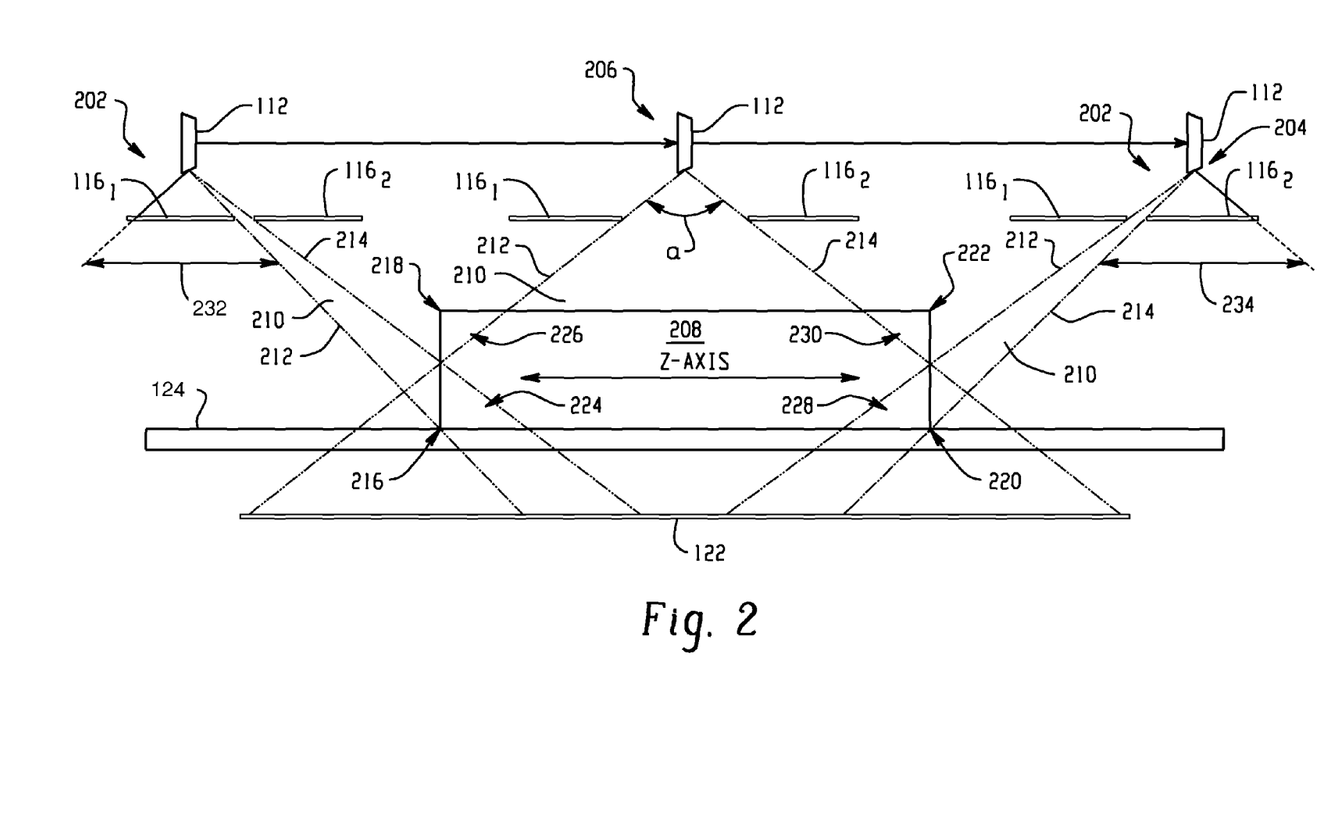
FIG. 2 illustrates example collimator blade motion during a fly-by scan.

As briefly described above, the at least one collimator blade 116 is configured so that it can dynamically translate in the z-axis direction, relative to the radiation source 112, during a fly-by scan. FIG. 2 illustrates example collimator blade motion with respect to a moving radiation source 112 during a fly-by scan and corresponding radiation beam geometry with respect to a region of interest. For clarity and explanatory purposes, the radiation source 112 is graphically represented via the anode of the radiation source 112 and the collimator 114 is omitted in FIG. 2.

In this example, the radiation source 112 moves from an initial or first position 202 to a destination or second position 204 through an intermediate position 206 while scanning a region of interest (ROI) 208 disposed on the patient support 124. The first and second positions 202 and 204 may represent the extent of travel or a subset thereof. Of course, the radiation source 112 may additionally or alternatively move in the opposite direction, for example, from the second position 204 to the first position 202.

For explanatory purposes, in the following discussion the position of the blades 116 is referenced with respect to the intermediate position at which the blades 116 are position so that emitted radiation is collimated to produce a radiation beam 210 with first and second outer projections or rays 212 and 214 and a suitable beam angle $\alpha$ for illuminating the ROI 208 and a desired extent of the detector array 122.

At the first position 202, the blade $116_1$ is positioned with respect the radiation source 112 to cone down or narrow the radiation beam 210, relative to the radiation beam 210 produced at the intermediate position, so that the first outer projection 212 crosses corners 216 and 218 of the ROI 208 as the radiation source 112 rotates about the z-axis 106.

As the radiation source 112 moves from the first position 202 to the intermediate position 206, the blade $116_1$ translates in an opposing direction. As a result, the aperture of the collimator 114 widens, coning up or increasing the width or beam angle of the radiation beam in the z-axis direction. The blade $116_1$ translates at a rate which ensures that the corners 216 and 218 and regions 224 and 226 are within the beam 210.

At the intermediate position 206, the blades 116 are positioned relative to the radiation source 112 so that the corners 216 and 218, the regions 224 and 226, corners 220 and 222, and regions 228 and 230 of the ROI 208 are illuminated by the radiation beam 210 as the radiation source 112 rotates about the z-axis 106.

As the radiation source 112 moves from the intermediate position 206 to the second position 204, the blade $116_2$ translates in an opposing direction. As a result, the aperture of the collimator 114 narrows, coning down or decreasing the width and beam angle of the radiation beam in the z-axis direction. The blade $116_2$ translates at a rate which ensures that the regions 228 and 230 are within the beam 210.

At the second position 204, the blade $116_2$ is positioned with respect the radiation source 112 to cone down the radiation beam 210, relative to the radiation beam 210 produced at the intermediate position 206, so that the second outer projection 214 crosses corners 220 and 222 of the ROI 208 and the radiation beam 210 illuminates the detector array 122 as the radiation source 112 rotates about the z-axis 106.

Positioning the blades 116 as such ensures that a complete set of data for the ROI 208 (at least 180 degrees plus a fan angle of data) is captured for reconstruction. In addition, radiation that would otherwise not be used for reconstruction, for example, radiation that traversing regions outside of the ROI 208 such as regions 232 and 234 if the collimator blades 116 were not positioned as such, is prevented from traverses the examination region 108. As such, patient dose may be reduced relative to a configuration in which the blades 116 do not cone down the beam 210 as the radiation source 112 nears either end of travel.

FIG. 3 further illustrates coning down of the beam as the radiation source 112 moves from the intermediate position 206 to the first position 202.

Figure 3A:
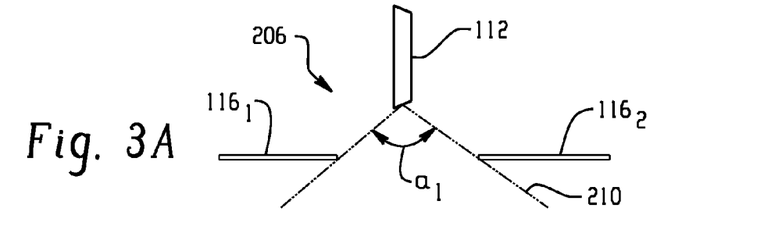
FIGS. 3A, 3B, 3C, 3D and 3E illustrate example collimator blade motion during a fly-by scan.

Initially referring to FIG. 3A, the radiation source 112 is at the intermediate position 206, and the blades 116 are positioned with respect to the radiation source 112 to define the beam 210 with a first beam angle $\alpha_1$ set in accordance with the ROI 208 and the detector array 122.

Figure 3B:
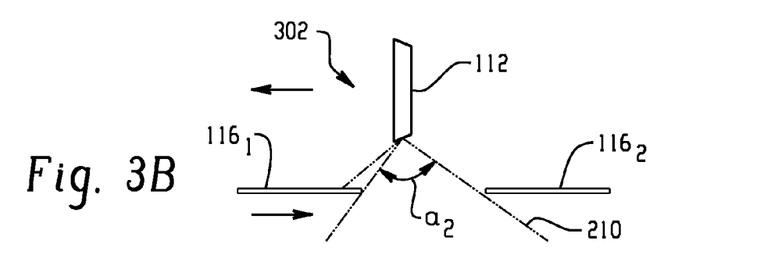

Turning to FIG. 3B, the radiation source 112 and collimator 114 are passing through a second intermediate position 302. During the translation, the collimator blade $116_1$ translates in the opposite direction of the radiation source 112 and collimator 114, narrowing the collimator aperture while ensuing that a complete data set is acquired, and the beam angle reduces to an angle $\alpha_2$.

Figure 3C:
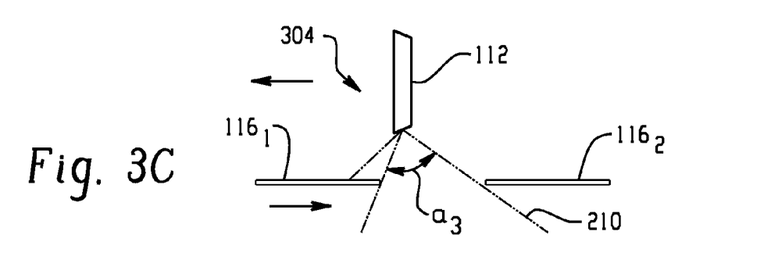

Next in FIG. 3C, the radiation source 112 and collimator 114 are passing through a third intermediate position 304. Again, during the translation the collimator blade $116_1$ translates in the opposite direction, further narrowing the collimator aperture. As a result, the beam angle reduces to angle $\alpha_3$.

Figure 3D:
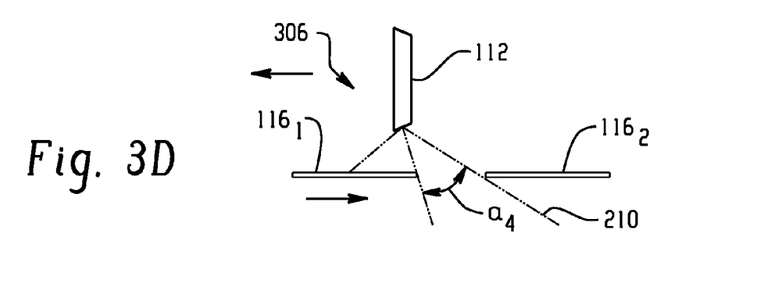

In FIG. 3D, the radiation source 112 and collimator 114 are passing through a fourth intermediate position 306. Likewise, during the translation the collimator blade $116_1$ translates in the opposite direction, further narrowing the collimator aperture. At the fourth intermediate position 306, the beam angle is narrowed to angle $\alpha_4$.

Figure 3E:
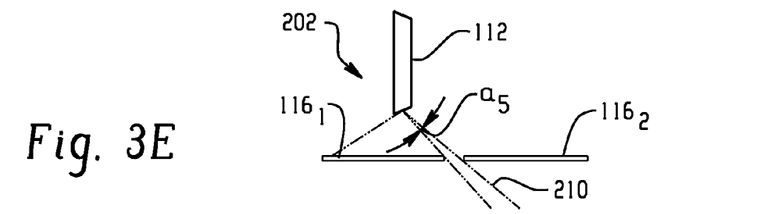

FIG. 3E shows the radiation source 112 and collimator 114 at the first position 202. At this position, the beam angle has been narrowed to angle $\alpha_5$ while satisfying the conditions described in connection with FIG. 2. Of course, the illustrated beam angle at the first position 202 is illustrative, and may be greater or smaller, including an angle (e.g., $\alpha=0$) in which no radiation traverses the examination region 108 or all or a substantial amount of the radiation is collimated.

It is to be understood that the above illustrates a sample of five snapshots in time during translation of the radiation source 112 and collimator 114 from the intermediate position 206 to the first position 202 as the collimator blade $116_1$ cones down the beam. As noted above, the collimator blade $116_1$ similarly cones down the beam as the radiation source 112 and collimator 114 translate from the intermediate position 206 to the second position 204. In addition, the collimator blades 116 cone up the beam as the radiation source 112 and collimator 114 translate from the first and second positions 202 and 204 to the intermediate position 206.

It is also to be appreciated that the movement of either or both of the blades 116 may be continuous or intermittent as the radiation source 112 and collimator 114 translates. Furthermore, the rate at which either or both of the blades 116 moves may be constant or variable.

Figure 4:
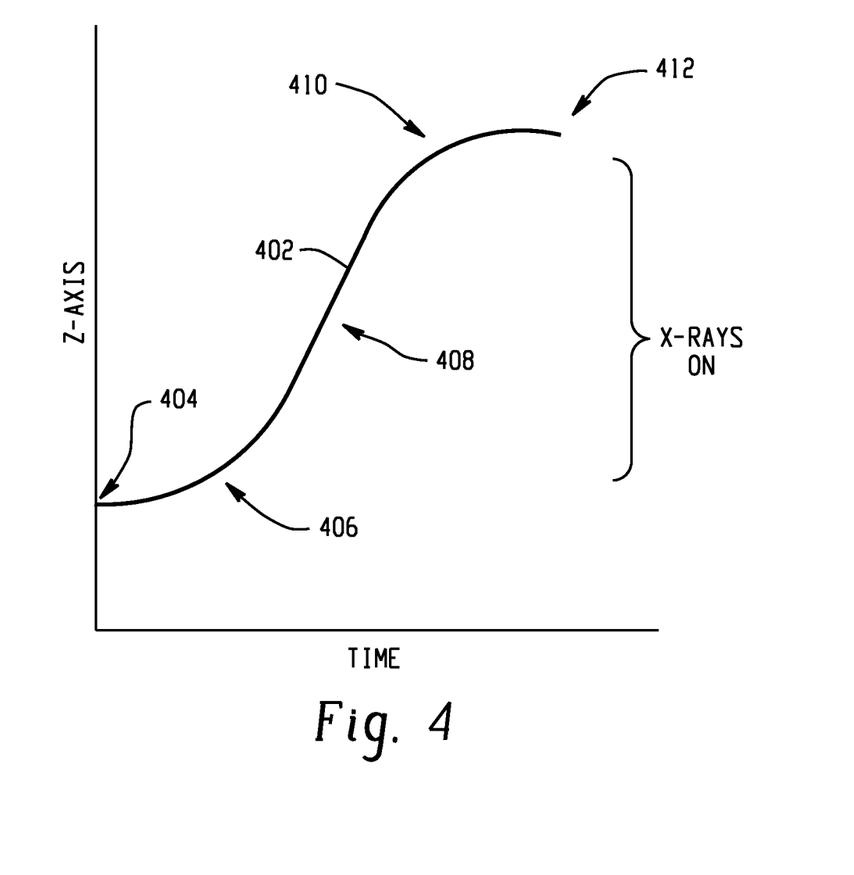
FIG. 4 illustrates an example fly-by scanning timing diagram for the collimator blade motion shown in FIGS. 2 and 3.

FIG. 4 graphically illustrates movement of the radiation source 112 along a path 402 during a fly-by scan using the approach described in connection with FIG. 2. The radiation source 112 is at an initial position 404 of the path 402 until a trigger signal such as a start scan signal is received while the rotating gantry portion 104 and, hence, the radiation source 112 rotates. When the trigger is received, the radiation source 112 accelerates through a first non-linear portion 406 of the path 402, during which x-rays are turned on. Then, the radiation source 112 traverses a second substantially linear portion 408 of the path 402 at about a constant speed. During a third non-linear portion 410 of the path 402, the radiation source 112 decelerates to a destination position 412 and x-rays are turned off. As the radiation source 112 moves through the path 402, the collimator blades 116 are dynamically adjusted as described in connection with FIG. 2 so that a complete set of data is captured. The variable speeds are taken into account during reconstruction.

It is to be appreciated that x-rays may or may not be on for the entire length of the path 402, for example, where the extent of the ROI in the z-axis direction is such that a complete set of data can be captured without scanning over the entire path 402. It is also noted that the x-rays may be on and data may be captured during the linear 408 or the path or both the linear 408 and the non-linear portions 406, 410 of the path 402. In addition, the trigger event may be electrical signal indicative of a state of the heart or a state of an agent ingested by the patient. Moreover, the radiation source 112 can make multiple passes along the path, in the same or alternate direction, for a procedure, for example, for a cardiac scan in which a same state of the heart is scanned multiple times.

Figure 5:
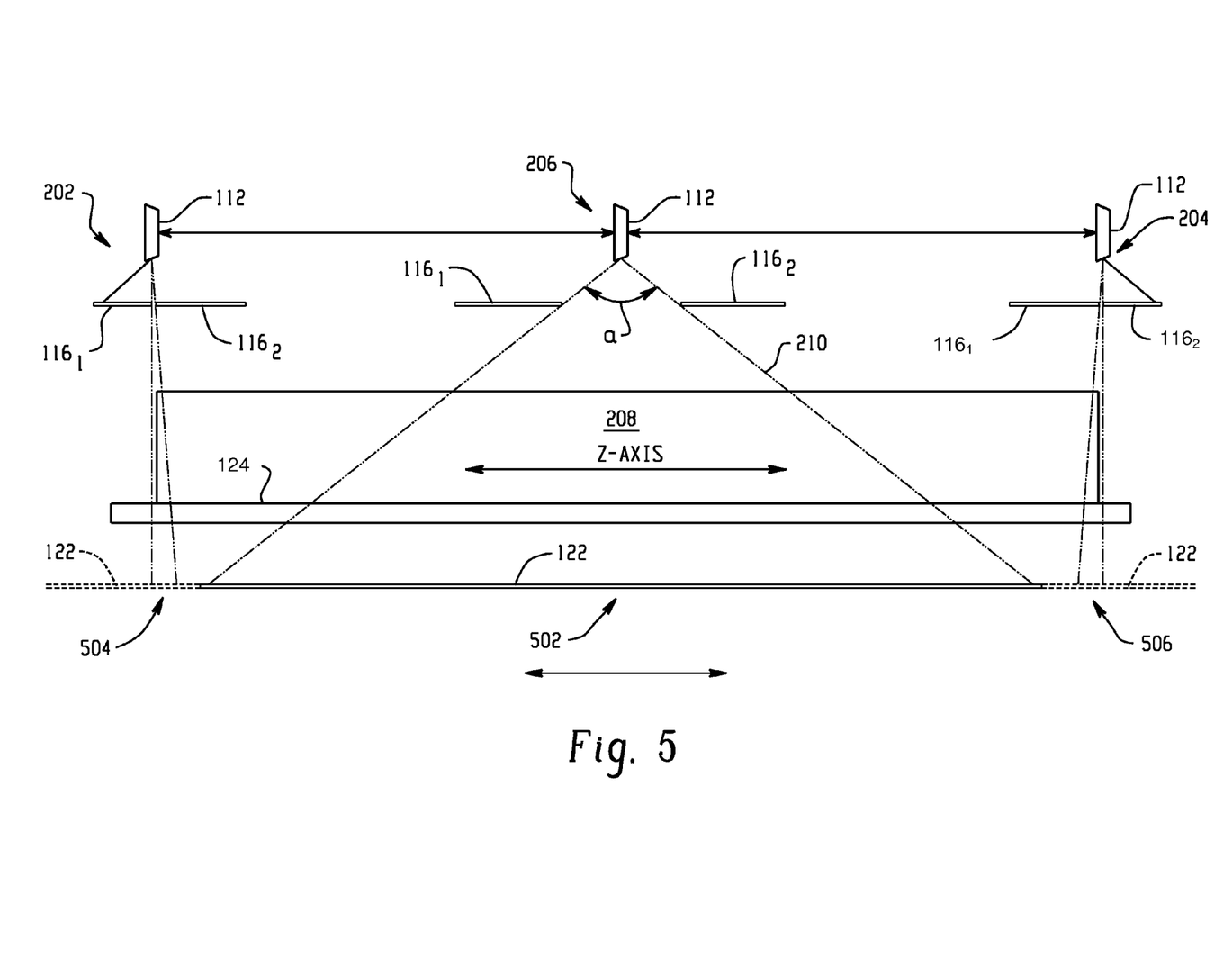
FIG. 5 illustrates example collimator blade motion during a fly-by scan.

FIG. 5 illustrates another example of dynamic collimation for fly-by scanning and corresponding radiation beam geometry. With the embodiment described in connection with FIG. 2, one of the blades 116 translates with respect to the radiation source 112 and the detector array 122 is stationary. In this example, the blades 116 concurrently translate with respect to the radiation source 112 and the detector array 122 translates therewith.

At the intermediate position 206, the detector array 122 is at a position 502 and the blades 116 are positioned relative to the radiation source 112 so that the radiation beam 210 illuminates the entire or a substantial portion of a z-axis width of the detector array 122, while minimizing irradiating regions outside of the z-axis width of the detector array 122. In one instance, at this position the beam 210 is centered about a mid section of the detector array 122.

As the radiation source 112 moves from the intermediate position 206 to the first position 202, both blades $116_1$ and $116_2$ translate, with respect to the radiation source 112, toward each other to cone down the beam 210. Concurrently, the detector array 122 moves towards the first position 202 in coordination with the radiation source 112 to a position 504. The pitch is also reduced in coordination with movement of the blades 116 and detector array 122. In one instance, the detector array 122 moves so that the beam 210 is centered about the mid section of the detector array 122 as the beam 210 moves to the first position 202. In this example, at the first position 202 the blade $116_1$ is positioned with respect the radiation source 112 such that an outside end ray of the beam 210 is substantially vertical or perpendicular with respect to the detector array 122, the detector array 122 is at the position 504, and the beam 210 is centered about the mid section of the detector array 122.

As the radiation source 112 moves from the intermediate position 206 to the second position 204, both blades $116_1$ and $116_2$ translate, with respect to the radiation source 112, toward each other to cone down the beam 210. Concurrently, the detector array 122 moves towards the first position 202 in coordination with the radiation source 112 to a position 506, and the pitch is also reduced in coordination with movement of the blades 116 and detector array 122. Likewise, in one instance the detector array 122 moves so that the beam 210 is centered about the mid section of the detector array 122 as the beam 210 moves to the second position 204. At the second position 204, the blade $116_1$ is positioned with respect the radiation source 112 such that an outside end ray of the beam 210 is substantially vertical or perpendicular with respect to the detector array 122, the detector array 122 is at the position 506, and the beam 210 is centered about the mid section of the detector array 122.

When moving from either position 202 or 204 to the intermediate position 206, both blades 116₁ and 116₂ translate, with respect to the radiation source 112, away from another to cone up the beam 210, and the detector array 122 concurrently moves towards the position 502. In this instance, the pitch is increased in coordination with movement of the blades 116 and detector array 122. As noted above, at the intermediate position 206, the detector array 122 is at a position 502 and the blades 116 are positioned relative to the radiation source 112 so that the radiation beam 210 is centered about a mid section of the detector array 122 and illuminates the entire or a substantial portion of a z-axis width of the detector array 122, while minimizing irradiating regions outside of the z-axis width of the detector array 122.

Positioning the blades 116 and detector array 122 and adjusting the scan pitch as such during a fly-by scan facilitates maximizing scan coverage. In addition, it ensures that a complete set of data for the ROI 208 is captured for reconstruction, while minimizing patient dose relative to a configuration in which the blades 116 do not cone down the beam 210 as the radiation source 112 nears either end of travel.

Figure 6:
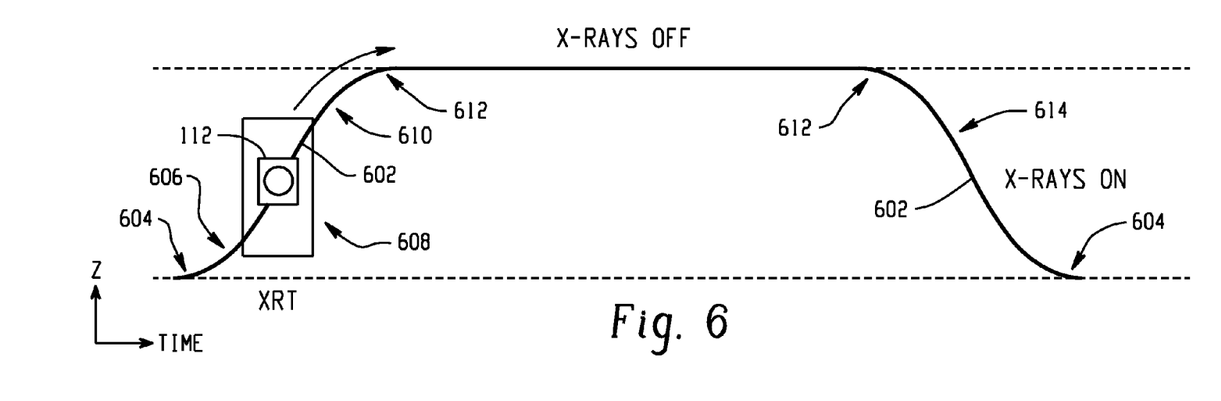
FIG. 6 illustrates an example fly-by scanning timing diagram for the collimator blade motion of FIG. 5.

FIG. 6 graphically illustrates movement of the radiation source 112 along a path 602 during a fly-by scan using the approach described in connection with FIG. 5. The radiation source 112 is at an initial position 604 of the path 602 until a trigger signal such as a start scan signal is received. When the trigger is received, x-rays are turned on and the radiation source 112 accelerates through a first non-linear portion 606 of the path 602, traverses a second substantially linear portion 608 of the path 602, and decelerates through a third non-linear portion 610 of the path 602 to a destination 612 position of the path 602. As the radiation source 112 moves through the path 602, the collimator blades 116 are dynamically adjusted as described in connection with FIG. 5. Once at the destination position 612, x-rays can be turned off until the next fly-by scan.

Figure 7:
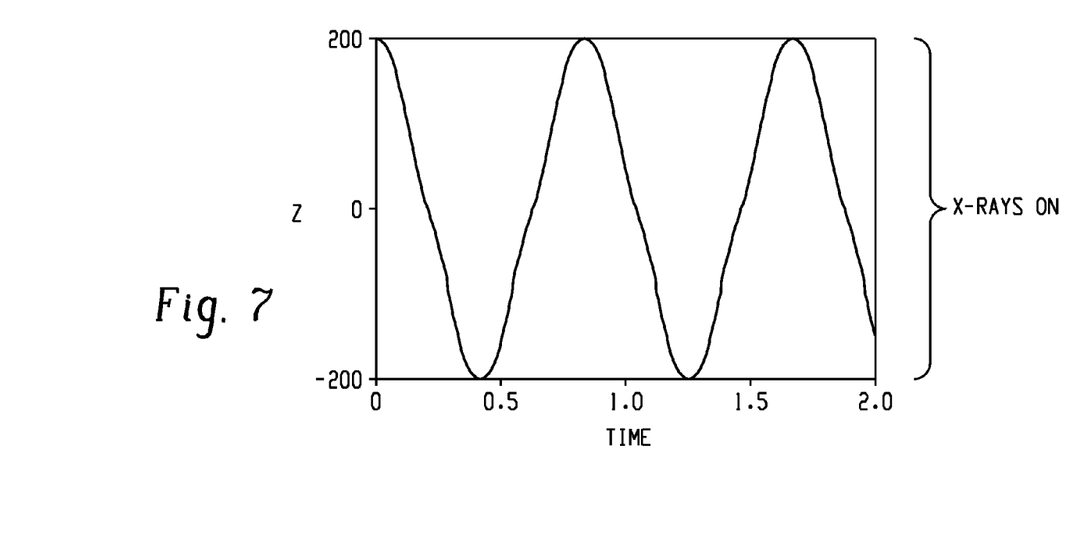
FIG. 7 illustrates continuous fly-by motion back and forth along the z-axis.

As illustrated in FIG. 6, for a subsequent scan at 614, the radiation source 112 moves in the opposite direction along the path 602 from the position 612 to the position 604. In one instance, this is used when performing multiple scans to capture the data for a moving object. For example, for a cardiac scan where multiple scans of the same cardiac phase are performed, the radiation source 112 may pause between scans in order to capture the same cardiac phase. In an alternative embodiment, the radiation source 112 is moved back to position 604 prior to performing a subsequent fly-by scan. In another embodiment, the radiation source 112 continuously travels back and forth along the path 602 with x-rays turned on during a procedure in which multiple passes are used to capture data. This is graphically shown in FIG. 7, which shows the radiation source 112 continuously translating back and forth along the z-axis over forty (40) centimeters (cm) while x-rays are turned on.

As noted above, concurrently coning down the radiation beam and varying the pitch allows for a relatively smaller cone angle at the ends of travel in order to increase coverage and capture a complete data set for reconstruction. The followings equations can be used to describe the scan frequency and coverage achieved by motion described by a sinusoid:

$$F := \frac{2}{\pi \cdot ST} \cdot \operatorname{asin}\left(\frac{Wd \cdot PF}{2 \cdot NSM}\right)$$

-continued $$C := \frac{NSM}{2} \cdot \left[\cos\left(\frac{1-FOT}{2} \cdot \pi\right) + \cos\left[\left(\frac{1-FOT}{2} + ST \cdot F\right) \cdot \pi\right]\right],$$

wherein F is the scan frequency, C is the scan coverage, ST is the scan time per gantry rotation, Wd is the isocenter width of the detectors, PF is the maximum pitch factor, NSM is the net source motion of the source, and FOT is the fraction x-ray on time.

By way of non-limiting example, for sinusoidal motion with NSM=400 mm, Wd=160 mm, FOT=1, PF=1.7, and ST=0.27 seconds, the achievable coverage C is about 350 mm with a x-ray motion frequency F of about 0.81 Hz. The reconstructable field of view (FOV) is about 250 mm, and the entire scan takes less than 0.62 seconds. For cardiac applications, the fraction x-ray on-time needs to be only 0.5 to cover 160 mm. The G-force for this trajectory is about 0.53 g. A pilot scan of over 350 mm can be performed in the same amount of time (0.62 scans), (or slightly longer depending on the maximum cone-size chosen for performing the pilot scan). The image quality is consistent throughout the scan since the cone-beam exposure adjusts to the pitch.

Figure 8:
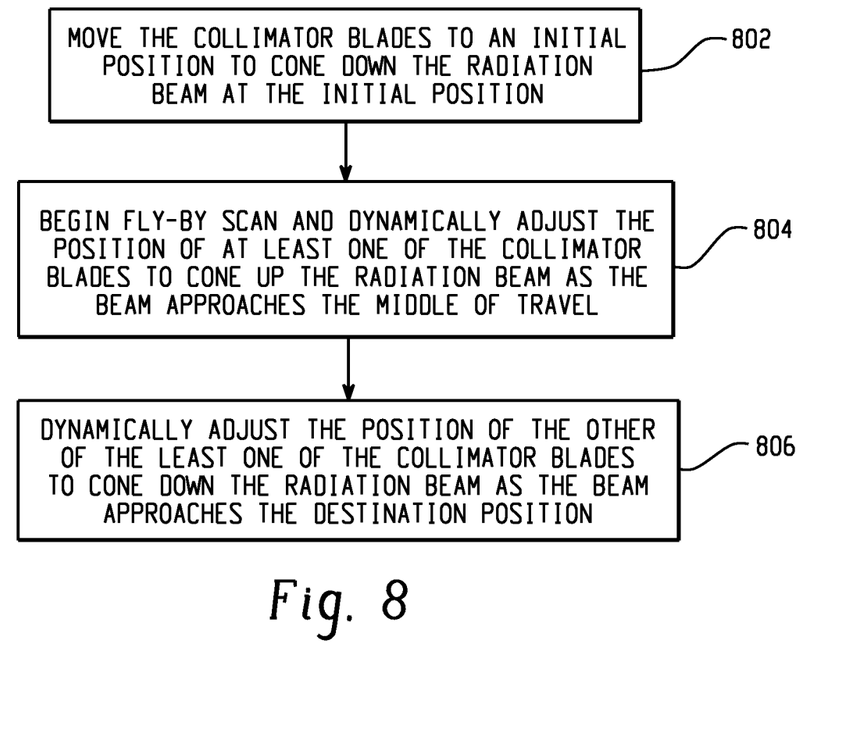
FIG. 8 illustrates an example method.

FIG. 8 illustrates a method for scanning with the system 100. At reference numeral 802, the radiation source 112 is rotating about at an initial position on the z-axis 106, and the collimator blades 116 are positioned so that when x-rays are turned on, the radiation beam is coned down so that the beam illuminates the ROI 208 while minimizing irradiating the patient with x-rays that are not used for reconstruction. At 804, the radiation source 112 and collimator 114 begins to translate in the z-axis direction and at least one of the collimator blades 116 dynamically adjusts to cone up or increase the beam angle as the beam approaches the middle of travel in a manner that ensures a complete set of data is acquired while continuing to minimize patient dose. At 806, as the radiation source 112 and collimator 114 approach the destination position, at least one of the collimator blades 116 dynamically adjusts to cone down or decrease the beam angle in a manner that ensures a complete set of data is acquired while continuing to minimize patient dose. It is to be appreciated that a subsequent fly-by scan can be performed by translating the radiation source 112 back along the path 412 or be first moving the radiation source 112 back to the initial position 404 and then repeating the acts 802-806.

Figure 9:
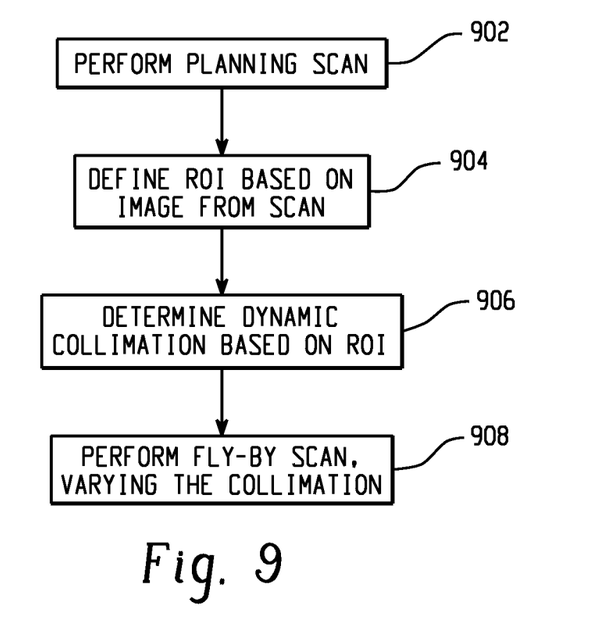
FIG. 9 illustrates operation of the imaging system.

Operation is described in connection with FIG. 9. At 902, a planning scan such as a pilot scan is performed. It is to be appreciated that for the pilot scan, the patient support 124, the radiation source 112, or a combination thereof translate along the z-axis. At 904, a region of interest (ROI) to be scanned is determined based on the pilot scan. For example, an operator may select during planning scan start and end points, which define the ROI, based on an image generated from the pilot scan. In one instance, a maximum extent of the ROI is limited based on a z-axis width of the detector array 112. At 906, the start and end points, the extent of the ROI, as well as other parameters corresponding to the scanning protocol, are used to determine suitable dynamic collimation and when x-rays are turned on and off for the scan. At 908, the fly-by scan is initiated, and the radiation source 112 translates, x-rays are turned on, and the source collimator 114 dynamically adjusts as the radiation source 112 translates as described herein. X-rays are then turned off, and the radiation source 112 decelerates to a destination position.

The above may be used in various applications including application where it may be desirable to achieve relatively large coverage (e.g., 35 cm) in a relatively short period of time without moving the patient support such as for cardiac, trauma, perfusion and/or other applications.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described various embodiments, the invention is now claimed to be:

1. An imaging system, comprising:
a radiation source that rotates around an examination region about a longitudinal axis and emits radiation while translating in a direction of the longitudinal axis during a fly-by scan in which the radiation source physically translates in the direction of the longitudinal axis during the scan;
a source collimator that translates in coordination with the radiation source and that collimates the emitted radiation during the fly-by scan to form a generally conical shaped radiation beam that traverses the examination region, wherein the source collimator dynamically varies a collimation during the scan so as to increase and decrease a width of the radiation beam in the direction of the longitudinal axis during the scan;
a detector array that detects radiation that traverses the examination region and generates signals indicative thereof, wherein the radiation source physically translates in the direction of the longitudinal axis during the scan relative to the detector array; and
a reconstructor that reconstructs the signals to generate volumetric image data indicative of the examination region.

2. The system of claim 1, wherein the dynamically varying the collimation allows at least 180 degrees plus a fan angle of data to be acquired for a region of interest in the examination region for a 180 degree reconstruction.

3. The system of claim 1, further comprising a controller that varies a pitch, which is a distance the radiation source travels per revolution of the radiation source, in coordination with the width of the radiation beam.

4. The system of claim 1, wherein the source collimator substantially blocks radiation traversing paths that do not traverse a region of interest disposed in the examination region.

5. The system of claim 1, wherein the source collimator includes: at least one collimator blade configured to translate in the direction of the longitudinal axis, wherein the at least one collimator blade translates in a first direction to increase a size of an aperture of the source collimator, thereby increasing the width of the radiation beam, and in a second opposing direction to decrease the size of the aperture, thereby decreasing the width of the radiation beam.

6. The system of claim 5, wherein the at least one collimator blade translates relative to the radiation source and the source collimator.

7. The system of claim 5, wherein the source collimator further includes:
at least a second collimator blade configured to translate in the direction of the longitudinal axis, wherein the at least one and the at least second collimator blades independently translate.

8. The system of claim 7, wherein only one of the at least one and the at least second collimator blades translates at any given time.

9. The system of claim 7, wherein the at least one and the at least second collimator blades concurrently translate in opposite directions in coordination to cone down and cone up the radiation beam.

10. The system of claim 9, wherein the detector array translates in the direction of the longitudinal axis in coordination with the at least one and the at least second collimator blades.

11. The system of claim 5, wherein the at least one collimator blade translates relative to the source collimator.

12. The system of claim 1, wherein the radiation source continuously emits radiation during the fly-by scan.

13. The system of claim 1, wherein the source collimator physically translates in one direction up to about 40 centimeters.

14. An imaging method, comprising:
varying a beam angle of a radiation beam emitted by an x-ray tube translating along a z-axis direction as the x-ray tube along the z-axis direction during a fly-by scan, wherein the beam angle increases as the x-ray tube translates from an initial position to an intermediate position and decreases as the x-ray tube translates from the intermediate position to a destination position, wherein varying the beam angle of the radiation beam includes concurrently translating, in opposing directions, first and second collimator blades of a source collimator that translates along with the translating x-ray tube.

15. The method of claim 14, further including defining a region of interest to be scanned, wherein the beam angle dynamically varies based on the region of interest.

16. The method of claim 15, further comprising basing a z-axis extent of the region of interest on a z-axis width of a detector array.

17. The method of claim 15, wherein varying a beam angle comprises dynamically varying the beam angle so that a complete set of data for reconstruction is captured for the region of interest.

18. The method of claim 14, wherein varying a beam angle comprises dynamically varying the beam angle as the x-ray tube translates based on a z-axis width of a detector array.

19. The method of claim 14, further including varying the beam angle so that a substantial portion of the radiation beam traversing an examination region traverses a region of interest in the examination region.

20. The method of claim 14, further including varying a pitch of the radiation beam in coordination with varying the beam angle.

21. The method of claim 14, further including varying the beam angle only over a sub-portion of the fly-by scan.

22. The method of claim 14, wherein the beam angle reduces an amount of radiation traversing paths outside of a region of interest dispose in an examination region, thereby mitigating patient exposure to x-rays not used for reconstruction.

23. The method of claim 14, further comprising physically moving the x-ray tube in the z-axis direction.

24. A non-transitory computer readable storage medium containing instructions which, when executed by a computer, cause the computer to: selectively vary a size of an aperture of a radiation source collimator in a z-axis direction during a fly-by scan performed with a medical imaging system in which a radiation source and the radiation source collimator translate in coordination from an initial position to a destination position, wherein the aperture determines a beam geometry of a radiation beam traversing a region of interest disposed in an examination region of the system and the size of the aperture is varied by concurrently and asynchronously translating, in opposing directions, first and second collimator blades of the radiation source collimator.

25. The non-transitory computer readable storage medium of claim 24, wherein the instructions, when executed by the computer, further cause the computer to translate the first and the second collimator blades of the radiation source collimator relative to the radiation source, thereby varying the size of the aperture.

26. The non-transitory computer readable storage medium of claim 24, wherein the instructions, when executed by the computer, further cause the computer to translate the first and the second collimator blades of the radiation source collimator relative to the radiation source, thereby increasing and decreasing the size of the aperture and a beam angle of the radiation beam.

27. The non-transitory computer readable storage medium of claim 24, wherein the instructions, when executed by the computer, further cause the computer to translate the first and the second collimator blades of the radiation source collimator relative to the radiation source to incrementally decrease a beam angle as the radiation source collimator approaches a limit of travel.

28. The non-transitory computer readable storage medium of claim 24, wherein the instructions, when executed by the computer, further cause the computer to adjust a scan pitch in coordination with the size of the aperture.

29. The non-transitory computer readable storage medium of claim 24, wherein the instructions, when executed by the computer, further cause the computer to continuously translate the first and the second collimator blades as the radiation source continuously translates back and forth along the z-axis direction.

* * * * *